United States Patent
Dreyfuss et al.

(10) Patent No.: US 12,364,470 B2
(45) Date of Patent: Jul. 22, 2025

(54) TENSIONABLE KNOTLESS ANCHORS AND METHODS OF TISSUE REPAIR

(71) Applicant: Arthrex, Inc., Naples, FL (US)

(72) Inventors: Peter J. Dreyfuss, Naples, FL (US); Tal S. David, San Diego, CA (US)

(73) Assignee: Arthrex, Inc., Naples, FL (US)

( * ) Notice: Subject to any disclaimer, the term of this patent is extended or adjusted under 35 U.S.C. 154(b) by 546 days.

(21) Appl. No.: 17/673,206

(22) Filed: Feb. 16, 2022

(65) Prior Publication Data
US 2023/0255612 A1 Aug. 17, 2023

(51) Int. Cl.
*A61B 17/04* (2006.01)

(52) U.S. Cl.
CPC .. *A61B 17/0401* (2013.01); *A61B 2017/0409* (2013.01); *A61B 2017/0414* (2013.01); *A61B 2017/0445* (2013.01); *A61B 2017/0464* (2013.01)

(58) Field of Classification Search
CPC ........ A61B 17/0401; A61B 2017/0409; A61B 2017/0414; A61B 2017/0445; A61B 2017/0464; A61B 2017/0466; A61B 17/0469; A61B 2017/0472; A61B 2017/0477; A61B 17/0485; A61B 2017/0495; A61B 2017/0496; A61B 17/0642; A61B 2017/0646; A61B 2017/042; A61B 2017/0403;
(Continued)

(56) References Cited

U.S. PATENT DOCUMENTS

| 8,608,777 B2 | 12/2013 | Kaiser et al. |
| 8,672,968 B2 | 3/2014 | Stone et al. |
| 8,986,346 B2 | 3/2015 | Dreyfuss |

(Continued)

FOREIGN PATENT DOCUMENTS

| EP | 2698128 B1 | 7/2017 |
| WO | 2020256853 A1 | 12/2020 |
| WO | 2021155148 A1 | 8/2021 |

OTHER PUBLICATIONS

Invitation to pay additional fees for International Application No. PCT/US2023/010737 dated Mar. 29, 2023.
(Continued)

*Primary Examiner* — Diane D Yabut
*Assistant Examiner* — Bridget E. Rabaglia
(74) *Attorney, Agent, or Firm* — Potomac Law Group, PLLC

(57) ABSTRACT

Tensionable, knotless, self-locking surgical constructs and methods for surgical repairs are disclosed. A tensionable, knotless, self-locking surgical construct includes a flexible coupler (repair suture) and a plurality of shuttle/pull devices loaded onto a fixation device. The fixation device can be a knotless fixation device such as a knotless soft anchor, for example, an all-suture knotless anchor. The knotless surgical construct provides multiple passes of the flexible coupler itself (repair suture itself), to achieve the desired friction and to also create a reverse purchase resistance to loosening. The flexible coupler (repair suture) is passed around tissue two or more times (and subsequently through the cannulation of the anchor sheath two or more times) creating a stuffed friction effect. There is no cinching loop in the final repair.

14 Claims, 4 Drawing Sheets

(58) Field of Classification Search
CPC .... A61B 2017/0448; A61B 2017/0462; A61B 17/06166; A61B 2017/0406
USPC .................................................. 606/144, 145
See application file for complete search history.

(56) References Cited

U.S. PATENT DOCUMENTS

| | | | |
|---|---|---|---|
| 9,060,763 | B2 | 6/2015 | Sengun |
| 9,486,202 | B2 | 11/2016 | Ferguson |
| 9,486,204 | B1 | 11/2016 | Ferguson et al. |
| 9,486,211 | B2 | 11/2016 | Stone et al. |
| 9,498,204 | B2 | 11/2016 | Denham et al. |
| 9,572,655 | B2 | 2/2017 | Denham et al. |
| 9,801,708 | B2 | 10/2017 | Denham et al. |
| 9,833,230 | B2 | 12/2017 | Stone |
| 10,004,493 | B2 | 6/2018 | Stone et al. |
| 10,070,856 | B1 | 9/2018 | Black et al. |
| 10,092,288 | B2 | 10/2018 | Denham et al. |
| 10,136,886 | B2 | 11/2018 | Norton et al. |
| 10,265,060 | B2 | 4/2019 | Dooney et al. |
| 10,327,755 | B2 | 6/2019 | Feezor et al. |
| 10,335,136 | B2 | 7/2019 | Dooney et al. |
| 10,349,931 | B2 | 7/2019 | Stone |
| 10,398,428 | B2 | 9/2019 | Denham et al. |
| 10,517,587 | B2 | 12/2019 | Denham et al. |
| 2013/0110165 | A1 | 5/2013 | Burkhart et al. |
| 2013/0296931 | A1 | 11/2013 | Sengun |
| 2013/0296934 | A1 | 11/2013 | Sengun |
| 2014/0052179 | A1 | 2/2014 | Dreyfuss et al. |
| 2014/0249577 | A1 | 9/2014 | Pilgeram |
| 2014/0257382 | A1* | 9/2014 | McCartney ........ A61B 17/0485 606/232 |
| 2015/0173739 | A1 | 6/2015 | Rodriguez et al. |
| 2019/0038276 | A1 | 2/2019 | Jackson |
| 2019/0099258 | A1 | 4/2019 | Armington et al. |
| 2019/0223857 | A1 | 7/2019 | Sengun |
| 2019/0365366 | A1 | 12/2019 | Petry et al. |
| 2020/0187933 | A1 | 6/2020 | Kaiser et al. |
| 2020/0268502 | A1 | 8/2020 | Brunsvold et al. |
| 2021/0244402 | A1 | 8/2021 | Leffler |
| 2021/0275160 | A1 | 9/2021 | Snell et al. |
| 2021/0290217 | A1 | 9/2021 | Biedermann et al. |
| 2021/0353280 | A1 | 11/2021 | Black et al. |
| 2022/0096074 | A1 | 3/2022 | Denham et al. |
| 2023/0146316 | A1 | 5/2023 | Stone et al. |
| 2023/0338017 | A1 | 10/2023 | Lund |

OTHER PUBLICATIONS

International Search Report and Written Opinion for International Application No. PCT/US2023/010737 dated Jun. 23, 2023.
Examination report for Australian Patent Application No. 2023245612 issued on Jun. 12, 2025.

* cited by examiner

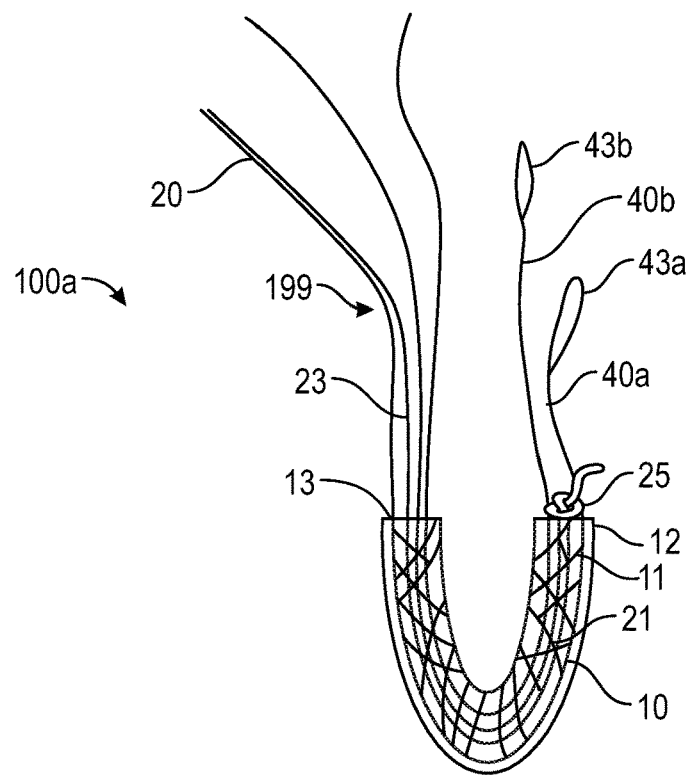
FIG. 1
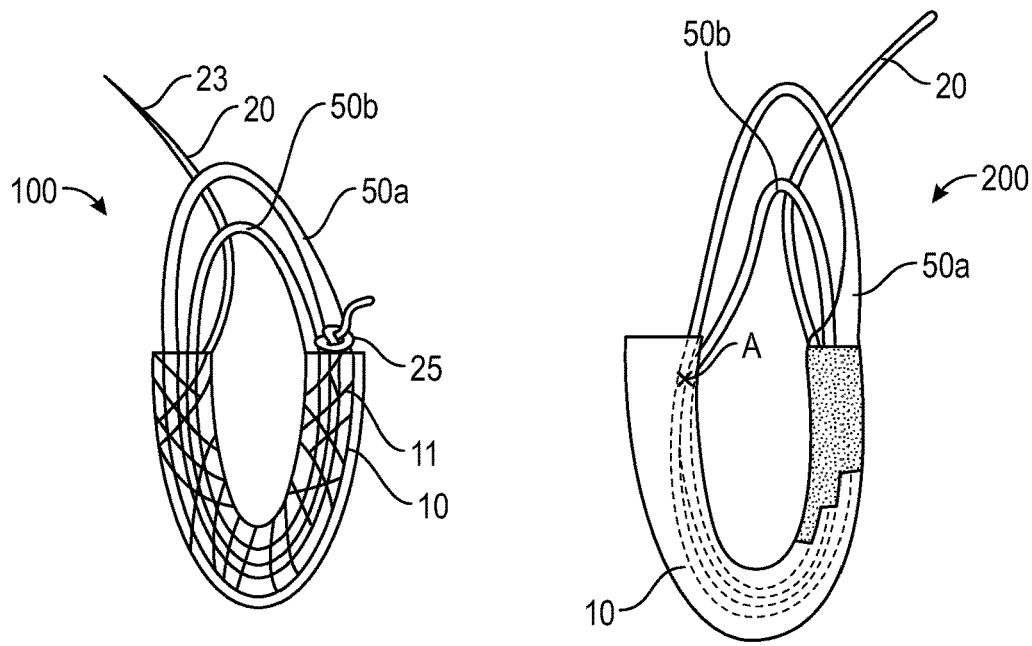
FIG. 2
FIG. 3

TENSIONABLE KNOTLESS ANCHORS AND METHODS OF TISSUE REPAIR

BACKGROUND

The disclosure relates to the field of surgery and, more specifically, to knotless anchor constructs and associated methods of tissue repairs.

SUMMARY

Reconstruction systems, assemblies, kits, and methods for fixation of soft tissue are disclosed.

A tensionable, knotless surgical construct can create a knotless, self-locking, reinforced repair. A tensionable, knotless, self-locking surgical construct includes a flexible coupler (repair suture) and a plurality of shuttle/pull devices loaded onto a fixation device. The fixation device can be a knotless fixation device such as a knotless soft anchor (for example, an all-suture knotless anchor) or a knotless soft anchor provided in a hard-body anchor. The knotless surgical construct may be employed in knotless fixation of first tissue to second tissue, for example, fixation of tendon to bone. The knotless surgical construct provides multiple passes of the flexible coupler (repair suture) itself, to achieve the desired friction and to also create a reverse purchase resistance to loosening. The flexible coupler (repair suture) is passed around tissue two or more times (and subsequently through the cannulation of the anchor sheath two or more times) creating a stuffed friction effect. There is no cinching loop in the final repair.

Methods of tissue repairs are also disclosed. In an embodiment, a knotless surgical construct provides tissue fixation without any knot formation, without any cinching or cinching loop formation, and with increased fixation and soft tissue compression without requiring stuffing of the anchor or friction.

BRIEF DESCRIPTION OF THE DRAWINGS

FIGS. 1-3 illustrate schematic views of surgical constructs.

DETAILED DESCRIPTION

Figure 4:
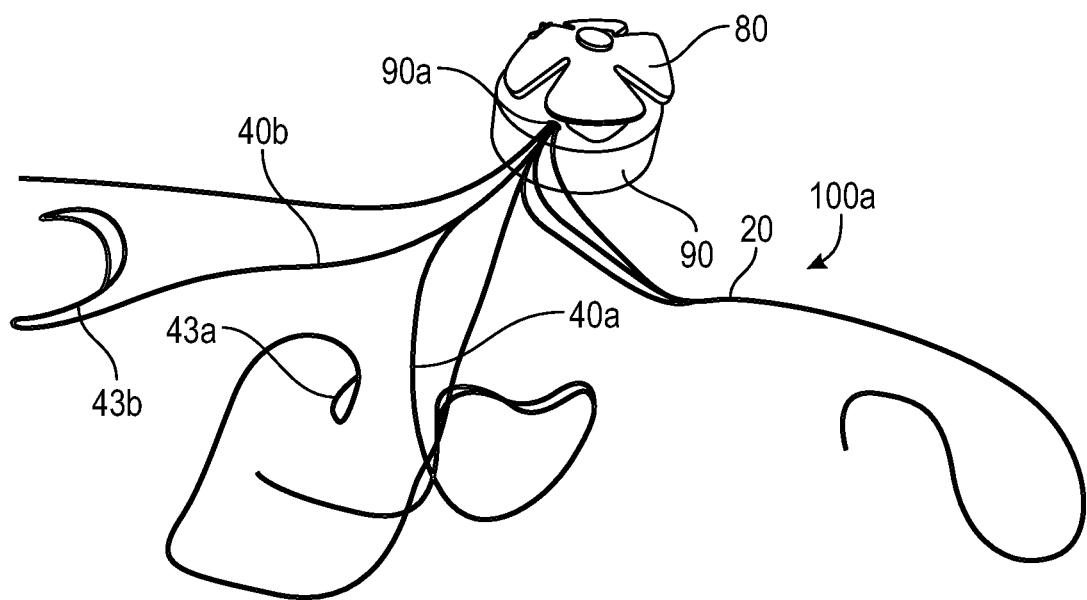
FIGS. 4-8 illustrate steps of a tissue repair with the surgical construct of FIG. 1.

A tensionable, knotless, self-locking surgical construct can create a knotless, reinforced repair.

A soft tissue repair system includes a tensionable, knotless, self-locking surgical construct with a fixation device and a flexible strand (flexible coupler) forming at least one self-locking, tensionable, knotless, independent mechanism loaded onto the fixation device. The self-locking, tensionable, knotless, mechanism includes a flexible coupler securely attached to the fixation device, and a plurality of shuttling devices for passing the flexible strand a plurality of times through the tissue to be secured and through the fixation device (i.e., one shuttling device for each pass desired). The fixation device can be a knotless fixation device such as a soft anchor, for example, an all-suture knotless anchor. The knotless surgical construct can be employed in knotless fixation of first tissue to second tissue, for example, fixation of soft tissue to bone.

Methods of knotless tissue repairs are also disclosed. In an embodiment, a surgical construct provides knotless tissue to tissue fixation, without any knot formation, and with increased fixation and soft tissue compression without requiring additional stuffing or increased friction to achieve final fixation. The methods allow formation of tissue repairs with increased strength and tissue compression. In an embodiment, a first tissue is approximated to a second tissue with a knotless, tensionable, self-locking, surgical construct that includes a tensionable, self-locking mechanism loaded onto a fixation device. The self-locking mechanism includes a flexible coupler and two or more shuttling devices. Knotless fixation is achieved by forming multiple passes to better create tissue apposition and improve tissue cut-through resistance (by way of reducing "cheese-wire" effect). The flexible coupler is passed multiple times through tissue and multiple times through the fixation device, building up a resistance to loosening of the final construct.

The disclosure provides surgical self-locking knotless surgical constructs, systems and assemblies, as well as methods for securing a first tissue to a second tissue, for example, knotless fixation of soft tissue (ligament, tendon, graft, etc.) to bone. The self-locking knotless surgical construct includes a fixation device with a tensionable construct (a self-locking mechanism) which forms multiple knotless, flexible, closed, loops (multiple passes) around the soft tissue to be secured to the bone.

Fixation devices (tensionable knotless anchors) are inserted into bone with a suture mechanism (a tensionable construct) formed of a flexible coupler provided within the fixation device (and attached to the fixation device) and with a plurality of shuttle/pull devices (shuttling devices or suture passing instruments) attached to the fixation device. After insertion of the fixation device within bone, the flexible coupler is passed through tissue to be secured to bone and through the body of the fixation device, multiple times, employing each of the plurality of shuttle/pull devices to form a plurality of passes. Each shuttle/pull device allows formation of an individual, separate pass of the flexible coupler, by passing the flexible coupler (repair suture) through the tissue and then through the fixation device.

The flexible coupler may include any flexible material, strand or ribbon such as suture or tape or combinations thereof, for example, multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). The flexible coupler may be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. Surgical constructs can be used with any type of flexible material or suture known in the art. The shuttle/pull device may be a suture passing instrument or a shuttle link such as a FiberLink™ or a Nitinol loop.

Referring now to the drawings, where like elements are designated by like reference numerals, FIGS. 1-8 illustrate exemplary surgical construct 100a, 100, 200 (surgical assembly 100a, 100, 200; surgical system 100a, 100, 200; tensionable, knotless construct 100a, 100, 200; tensionable, knotless, self-locking, surgical anchor 100a, 100, 200) including exemplary fixation device 10 with exemplary knotless, self-locking, tensionable mechanism 199 within a body of the fixation device 10.

Surgical construct 100a of FIG. 1 includes fixation device 10 preloaded with knotless, self-locking, tensionable mechanism 199 formed by a flexible coupler 20 (flexible strand 20; suture 20; repair suture 20) and two of more shuttle/pull devices 40*a*, 40*b* (suture passing instruments 40*a*, 40*b*; suture passers 40*a*, 40*b*; shuttle links 40*a*, 40*b*; FiberLinks™ 40*a*, 40*b*; nitinol loops 40*a*, 40*b*). Surgical construct 100 of FIG. 1 without the two of more shuttle/pull devices 40*a*, 40*b* and after formation of flexible, closed, knotless, continuous, adjustable loops 50*a*, 50*b*.

As shown in FIG. 1, fixation device 10 can be in the form of a soft anchor (soft suture anchor, or all-suture soft knotless anchor, or soft body suture anchor) provided with a soft anchor sleeve 11 (sheath or tubular member 11) with two open ends 12, 13. Flexible coupler 20 extends through the soft anchor sleeve (sheath). Two of more shuttle/pull devices 40*a*, 40*b* . . . 40*n* also extend through the sleeve, in similar or different directions and/or orientations and/or locations. Details of an exemplary soft suture anchor with a soft anchor sleeve (sheath or tubular member) and flexible shuttling strands are set forth, for example, in U.S. application Ser. No. 15/998,516 entitled "Methods of Tissue Repairs" filed on Aug. 16, 2018, the disclosure of which is incorporated by reference in its entirety herein. The flexible coupler and the plurality of shuttle/pull devices can extend through the sleeve in similar or different directions and/or orientations and/or locations.

Flexible coupler 20 is provided with two terminal ends, a first end 21 and a second end 23. The first end 21 is a fixed end that forms exemplary static knot 25 at distal end 12, and the second end 23 is a flexible end (free end 23) that exits open end 13 of the sheath 11, as shown in FIG. 1, for example. As detailed below, second end 23 will form a plurality of flexible, closed, knotless, continuous, adjustable loops 50*a*, 50*b*, 50*c* . . . etc. (referred to, for simplicity, as a "plurality of flexible, closed, knotless, continuous, adjustable loops 50") having an adjustable perimeter and adjustable length.

Two exemplary shuttle/pull devices 40*a*, 40*b* are attached to (passed through) the sheath 11 and simply reside side by side in the sheath. Shuttle/pull devices 40*a*, 40*b* are independent from each other and do not pass through one another or any other structure (other than the sheath 11). If more than two shuttle/pull devices 40*a*, 40*b*, 40*c* . . . etc. (referred to, for simplicity, as a "plurality of shuttle/pull devices 40") are employed, each of the plurality of shuttle/pull devices can reside within the sheath 11 independent from each other and without passing through one another or through any other structure (other than the sheath 11).

FIG. 1 illustrates two exemplary shuttle/pull devices 40*a*, 40*b* in the form of suture passing instruments or suture passers such as FiberLinks™ 40*a*, 40*b* or nitinol loops 40*a*, 40*b*, or combinations thereof, passed through the sheath 11 and non-attached to the flexible coupler 20, and prior to formation of any flexible, closed, knotless, continuous, adjustable loops. Each of suture passing devices 40*a*, 40*b* includes an eyelet/loop 43*a*, 43*b* for passing the flexible coupler 20.

FIG. 2 illustrates soft suture anchor 100 after formation of two exemplary flexible, closed, knotless, continuous, adjustable loops 50*a*, 50*b* (with the free end 23 of flexible coupler 20 and with each of the two exemplary shuttle/pull devices 40*a*, 40*b*).

FIG. 3 illustrates soft suture anchor 200 which is about similar to soft suture anchor 100 of FIG. 2 in that it also includes two exemplary flexible, closed, knotless, continuous, adjustable loops 50*a*, 50*b* formed with the free end 23 of flexible coupler 20 and with each of the two exemplary shuttle/pull devices 40*a*, 40*b*. However, soft suture anchor 200 differs in the way fixed end 21 of flexible coupler 20 is attached to the sheath 11, i.e., by a method other than knotting, for example, gluing. The free end 23 of the flexible coupler also exits the sheath 11 at a location A which is spaced from the opening end 13 of the sheath 11.

The flexible coupler 20 may be passed through at least a portion of the body of the fixation device 10 (for example, through a full cannulation of the fixation device, or may exit the body of the fixation device at a location other than most distal end and most proximal end of the fixation device).

As detailed below, subsequent to the insertion of fixation device 10 of surgical construct 100*a* into a drilled hole in bone, the flexible coupler 20 and shuttle/pull devices 40*a*, 40*b* are released from the driver, and the driver removed. Free end 23 of flexible coupler 20 is subsequently passed through the tissue 80 and then through the eyelet/loop 43*a* of first suture passing device 40*a*. Suture passing device 40*a* is then pulled, thereby pulling free end 23 of the flexible coupler 20 towards the body of the fixation device, inside of the sheath 11 and then exiting the sheath 11 to form a first flexible, closed, knotless, continuous, adjustable loop 50*a*. The suture end 23 of flexible coupler 20 is then passed again through tissue 80 and then through the eyelet/loop 43*b* of second suture passing device 40*b*. Suture passing device 40*b* is then pulled, thereby pulling free end 23 of the flexible coupler 20 towards the body of the fixation device, inside of the sheath 11 and then exiting the sheath 11 to form a second flexible, closed, knotless, continuous, adjustable loop 50*b*. These steps are repeated for the formation of n-loops 50 with the aid of corresponding n-suture passing devices 40.

FIGS. 4-8 illustrate schematic steps of a tissue repair 101 (e.g., tendon or ligament repair) with the surgical construct 100*a* of FIG. 1. FIGS. 4-8 illustrate only a schematic view of tissue 80 (for example, tendon) to be secured to bone 90. FIG. 4 illustrates tissue 80 before the passage of the flexible coupler 20 through it and with exemplary fixation device 10 of surgical construct 100*a* inserted and secured within a hole 90*a* of bone 90.

Figure 5:
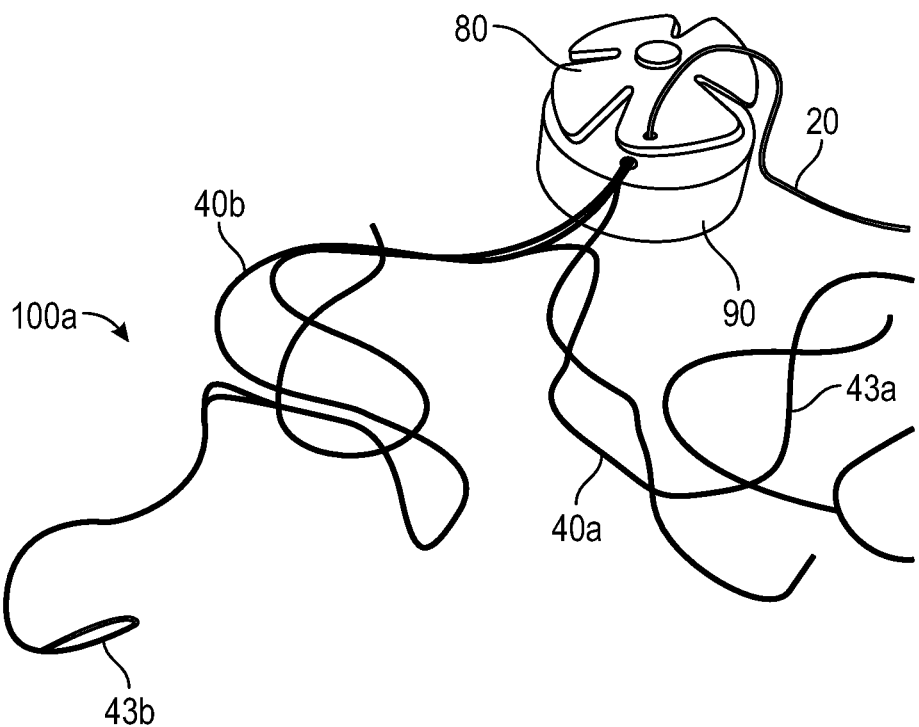
Figure 6:
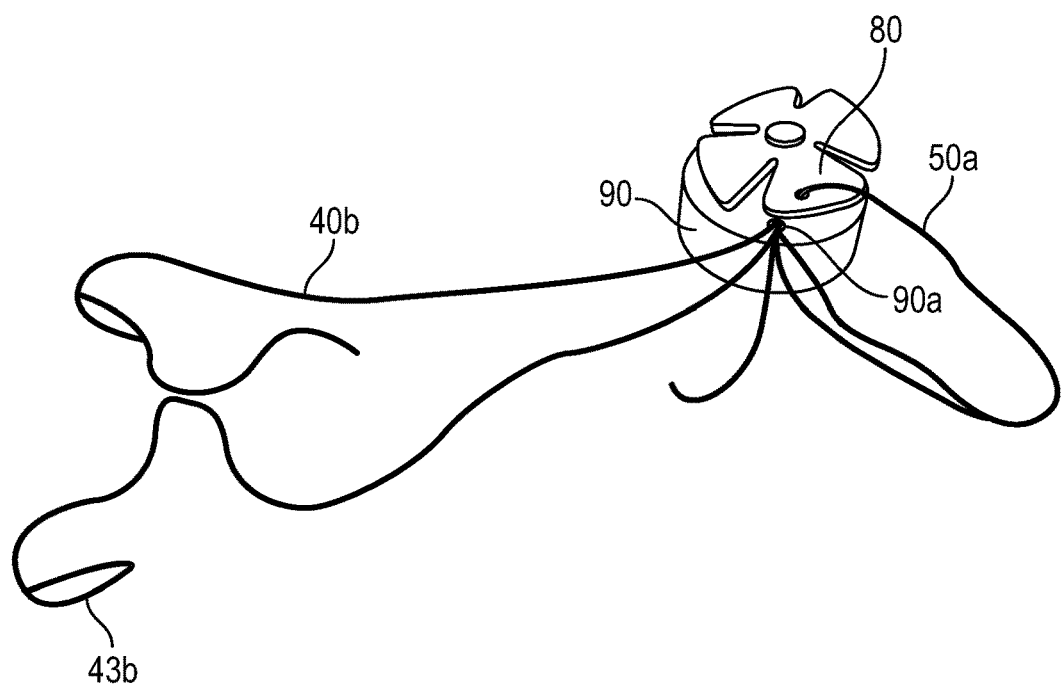
Figure 7:
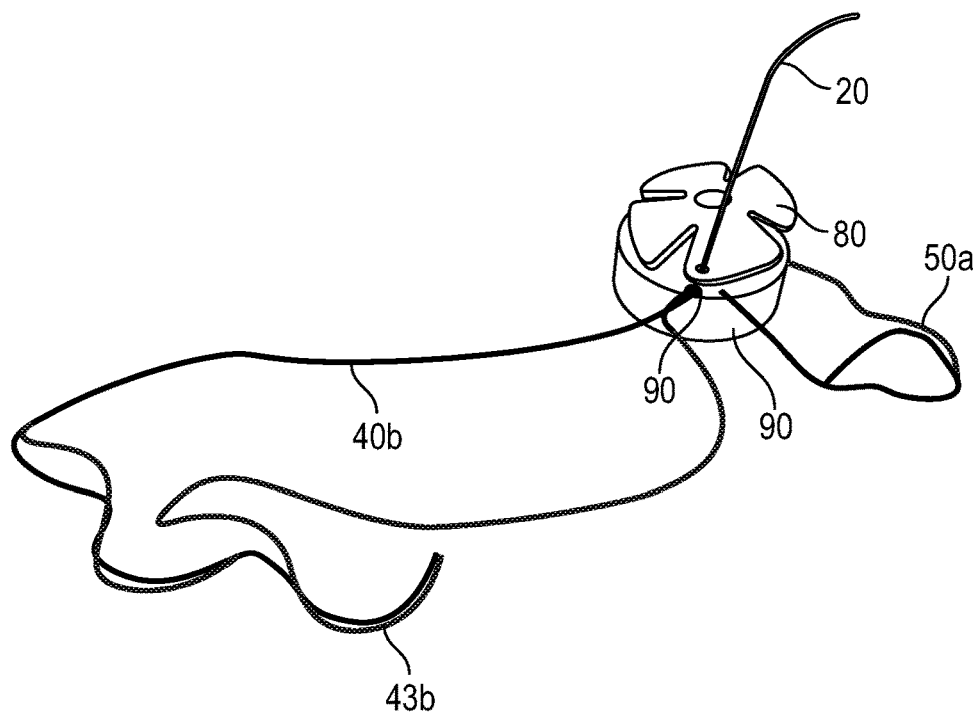

FIGS. 5-7 illustrate passage of the flexible end 23 of flexible coupler 20 through tissue 80 and then through eyelet 43*a* of first shuttle/pull device 40*a* to form a first flexible, closed, knotless, continuous, adjustable loop 50*a*. Once the flexible coupler 20 is passed through the through eyelet 43*a* of first shuttle/pull device 40*a*, the shuttle/pull device 40*a* is then pulled out of the fixation device 10 and out of the surgical site, to allow the flexible coupler 20 to pass through the sheath 11 of the fixation device 10 (without passing through itself and without forming any splice) to form a first flexible, tensionable, continuous, adjustable, self-locking, cinching, closed loop 50*a* (FIG. 8) around tissue 80.

Figure 8:
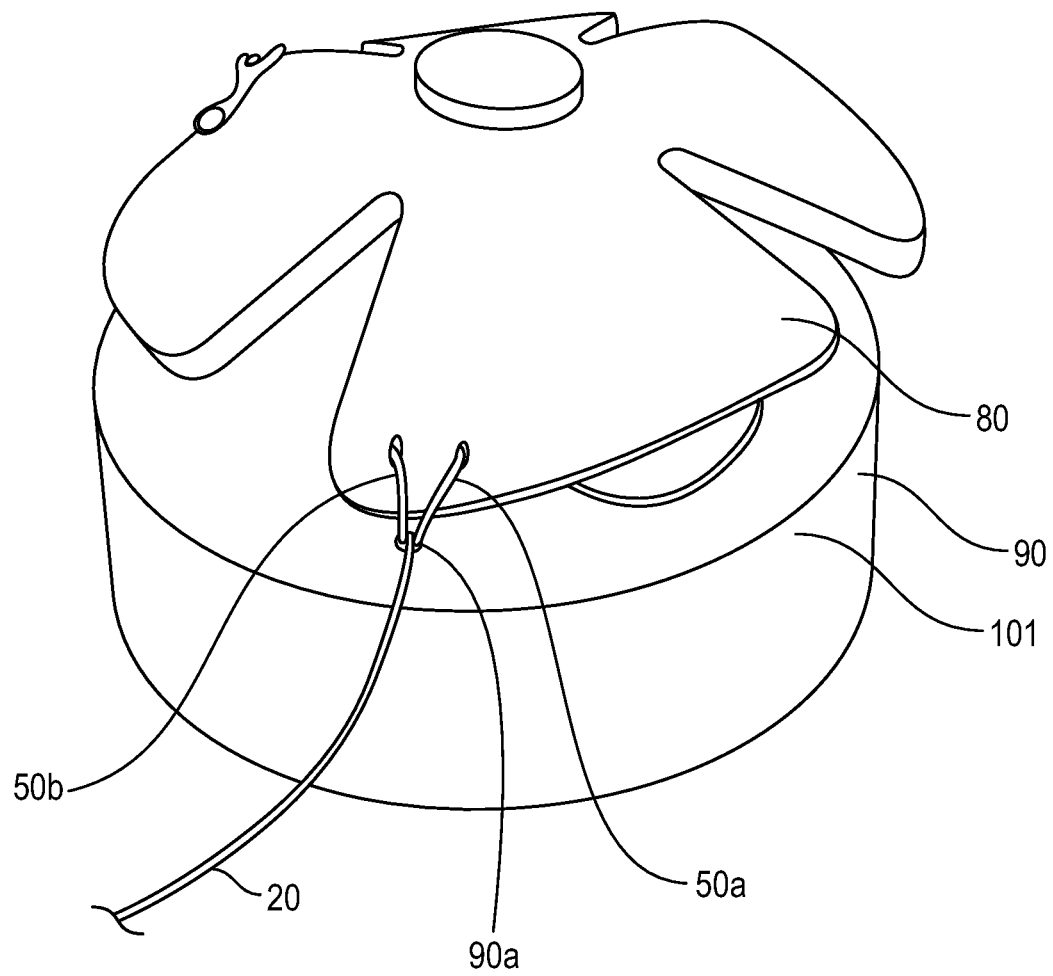

Free end 23 of the flexible coupler is passed again through tissue 80 and then through eyelet 43*b* of second shuttle/pull device 40*b* to form a second flexible, closed, knotless, continuous, adjustable loop 50*b* around the tissue 80. Once the flexible coupler 20 is passed through the through eyelet 43*b* of second shuttle/pull device 40*b*, the shuttle/pull device 40*b* is then pulled out of the fixation device 10 and out of the surgical site, to allow the flexible coupler 20 to pass through the sheath 11 of the fixation device 10 (without passing through itself and without forming any splice) to form a second flexible, tensionable, continuous, adjustable, self-locking, cinching, closed loop 50*b* (FIG. 8) around tissue 80 and as part of repair 101 (FIG. 8). Loops 50*a*, 50*b* have an adjustable length and perimeter.

Free end 23 of the flexible coupler 20 can be pulled to shrink the construct and the flexible, closed, knotless, continuous, adjustable loops 50*a*, 50*b*, and to compress the tendon to bone, providing a final repair/construct 101 with increased compression of tissue.

The constructs, systems, and assemblies of the present disclosure may be employed in numerous knotless soft tissue repairs and fixations, for example, fixation of soft tissue to bone. Although the embodiments above have been illustrated with reference to a double-loaded construct, i.e., a construct provided with two exemplary shuttle/pull devices, the disclosure is not limited to this exemplary-only embodiment and contemplates knotless self-locking tensionable constructs that are multiple-loaded constructs, i.e., including three or more knotless self-locking tensionable mechanisms and three or more corresponding shuttle/pull devices, to aid in increased tissue fixation and compression to bone.

Methods of soft tissue repair which do not require tying of knots and allow adjustment of both the tension of the suture and the location of the tissue with respect to the bone, while providing self-locking mechanism, are disclosed. A method of knotless tissue repair comprises inter alia the steps of: securing a fixation device 10 into a first tissue 90, the fixation device being preloaded with a flexible coupler 20 and with a plurality of shuttle/pull devices 40a, 40b; and passing the flexible coupler 20 through a second tissue 80 to be positioned relative to the first tissue 90 and then through the fixation device 10 by employing the plurality of shuttle/pull devices 40a, 40b, to form a plurality of adjustable, knotless, closed, continuous loops 50a, 50b around the second tissue 80.

Another exemplary method comprises inter alia the steps of: (i) providing a surgical construct 100a comprising a fixation device 10 (for example, an anchor 10) with a self-locking, tensionable, knotless mechanism 199 including a flexible coupler 20 (for example, suture 20) and two or more shuttle/pull devices 40a, 40b (two or more suture passing instruments) attached to the fixation device 10; (ii) inserting the fixation device 10 into a hole 90a formed within bone 90; (iii) passing the flexible coupler 20 through tissue 80 to be fixated (or reattached) to bone 90; (iv) passing the flexible coupler 20 through an eyelet/loop of a first shuttle/pull device 40a and, subsequently, pulling on the first shuttle/pull device 40a to allow the flexible coupler 20 to pass through the fixation device 10 and form a first knotless, closed, adjustable, flexible, continuous loop 50a around the tissue 80 and without forming any splice or cinching loop; (v) passing the flexible coupler 20 again through tissue 80 to be fixated (or reattached) to bone 90; (vi) passing the flexible coupler through an eyelet/loop of a second shuttle/pull device 40b and, subsequently, pulling on the second shuttle/pull device 40b to allow the flexible coupler 20 to pass again through the fixation device 10 and form a second knotless, closed, adjustable, flexible, continuous loop 50b around the tissue 80 and without forming any splice or cinching loop; and (vii) pulling on the flexible coupler 20 to adjust tension on the two loops 50a, 50b around tissue 80, to lock the construct, to allow the soft tissue to achieve the desired location relative to the bone, and to allow proper tensioning of the final repair/construct 101. The knotless, closed, adjustable, flexible, continuous loop 50a, 50b can have an adjustable perimeter.

As detailed above, when the anchor is inserted, the anchor has one repair suture limb (which is fixed at the anchor) and also shuttle links (two shuttle links, as in the embodiment above). The repair suture is passed thru tissue, and then shuttled thru the anchor. Then the step is repeated again (and again, if additional links are present). The final construct is the repair suture passing multiple times thru tissue, and multiple times thru the anchor. There is no splice, only the multiple passes thru the anchor and tissue which build up a resistance to loosening. There could be stuffing in the repair suture at a point which would add resistance when the construct is fully tensioned. The usage of multiple passes ultimately causes sufficient holding strength of the repair, without the need for splicing or additional stuffing.

Currently, prior art fixation systems/products rely on stuffing and/or friction (or similar mechanisms) to achieve fixation. The present disclosure relies on multiple passes of the repair suture itself in order to achieve the friction and also create the reverse purchase resistance to loosening. The disclosure provides a reverse purchase stuffed suture anchor, i.e., a "mechanical disadvantage" stuffed suture anchor. The repair suture is passed around tissue two or more times (and subsequently through the cannulation of the anchor sheath two or more times) creating a stuffed friction effect. Tensioning is therefore 2:1 purchase, whereas loosening is 1:2 resistance. There is no cinching loop in the final repair yet the multiple passes ultimately cause sufficient holding strength of the repair.

Flexible coupler 20 can be in the form of any elongated members, fibers, or materials, or combinations thereof. Flexible coupler 20 can include a single filament, or fiber, or can include multiple continuous filaments, segments or regions of filaments that have different configurations (for example, different diameters and/or different compositions). The filament regions/segments may each be homogenous (i.e., formed of a same material) or may be a combination of homogenous and heterogenous (i.e., formed of a plurality of materials). Exemplary materials may include suture, silk, cotton, nylon, polypropylene, polyethylene, ultrahigh molecular weight polyethylene (UHMWPE), polyethylene terephthalate (PET), and polyesters and copolymers thereof, or combinations thereof.

Flexible coupler 20 may be a high-strength suture, such as an ultrahigh molecular weight polyethylene (UHMWPE) suture which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM) fibers, braided with at least one other fiber, natural or synthetic, to form lengths of suture material.

Flexible coupler 20 can include any flexible materials or strands such as suture or tape, for example, multifilament, braided, knitted, woven suture, or including fibers of ultra-high molecular weight polyethylene (UHMWPE). The flexible coupler can be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. Surgical self-locking constructs can be used with any type of flexible material or suture known in the art.

Flexible coupler 20 can be also formed of a stiff material, or combination of stiff and flexible materials, particularly for the regions of the couplers that are passed/spliced through the body of the coupler and depending on whether they are employed with additional fixation devices. In addition, flexible coupler 20 can be also coated and/or provided in different colors for easy manipulation during the surgical procedure. The knotless constructs and self-locking soft anchors of the present disclosure can be used with any type of flexible material or suture that may be weaved or passed through itself.

Flexible coupler 20 and/or suture passing devices 40 may be also provided with tinted tracing strands, or otherwise contrast visually with the sheath of the construct, which remains a plain, solid color, or displays a different tracing pattern, for example. Various structural elements of surgical construct 100, 200 may be visually coded, making identification and handling of the suture legs simpler. Easy identification of suture in situ is advantageous in surgical procedures, particularly during arthroscopic surgeries, endoscopic and laparoscopic procedures.

The surgical constructs of the present disclosure may be employed in endoscopic surgery. The term "endoscopic surgery" refers to surgical procedures within a patient's body through small openings as opposed to conventional open surgery through large incisions. Additionally, surgical constructs as disclosed herein may be utilized in other general surgical and specialty procedures that soft tissue repairs.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed:

1. A method of knotless tissue repair comprising:
   securing a fixation device into a first tissue, the fixation device being preloaded with a flexible coupler and with a plurality of shuttle/pull devices, wherein the flexible coupler and the plurality of shuttle/pull devices extend through the fixation device; and
   subsequently, passing the flexible coupler through a second tissue to be positioned relative to the first tissue and then through the fixation device by employing the plurality of shuttle/pull devices, to form a plurality of knotless, closed, continuous loops around the second tissue.

2. The method of 1, wherein the plurality of knotless, closed, continuous loops are formed by passing the flexible coupler through the fixation device without forming any splice or any cinching loop.

3. The method of claim 1, further comprising:
   passing a limb of the flexible coupler through the second tissue and then through the fixation device by employing a first shuttle/pull device of the plurality of shuttle/pull devices, to form a first knotless, closed, continuous loop around the second tissue; and
   subsequently, passing the limb of the flexible coupler through the second tissue and then through the fixation device employing a second shuttle/pull device of the plurality of shuttle/pull devices, to form a second knotless, closed, continuous loop around the second tissue.

4. The method of claim 3, further comprising:
   pulling on the first shuttle/pull device to allow the limb of the flexible coupler to form the first knotless, closed, continuous loop around the second tissue but without passing the limb through the flexible coupler to form a splice; and
   pulling on the second shuttle/pull device to allow the limb of the flexible coupler to form the second knotless, closed, continuous loop around the second tissue but without passing the limb through the flexible coupler to form a splice.

5. The method of claim 1, wherein the fixation device is a soft-body anchor.

6. The method of claim 1, wherein the fixation device is a soft body anchor, the flexible coupler is secured to the fixation device by a knot, and wherein each of the plurality of shuttle/pull devices extends through a body of the fixation device.

7. The method of claim 1, wherein the first tissue is bone and the second tissue is tendon or ligament.

8. The method of claim 1, wherein each of the plurality of knotless, closed, continuous loops has an adjustable perimeter.

9. The method of claim 1, wherein the flexible coupler is suture or suture tape.

10. The method of claim 1, wherein at least one of the plurality of shuttle/pull devices is a suture with a closed loop on one end.

11. A method of forming a knotless, tensionable, self-locking repair, comprising:
    attaching a flexible coupler with a first end and a second end to a fixation device by securing the first end to the fixation device, wherein the flexible coupler extends through the fixation device;
    securing a plurality of shuttle/pull devices to the fixation device;
    securing the fixation device into a first tissue;
    passing the second end of the flexible coupler through a second tissue to be approximated to the first tissue;
    passing the second end of the flexible coupler through a closed eyelet of a first shuttle/pull device;
    pulling the first shuttle/pull device out of the fixation device to form a first loop around the second tissue, the first loop being a knotless, continuous, uninterrupted loop with an adjustable perimeter;
    subsequently, passing the second end of the flexible coupler through the second tissue;
    passing the second end of the flexible coupler through a closed eyelet of a second shuttle/pull device; and
    pulling the second shuttle/pull device out of the fixation device to form a second loop around the second tissue, the second loop being a knotless, continuous, uninterrupted loop with an adjustable perimeter.

12. The method of claim 11, wherein the first tissue is bone and the second tissue is soft tissue.

13. The method of claim 11, wherein the fixation device is a soft all-suture anchor.

14. The method of claim 11, wherein the knotless, tensionable, self-locking repair does not include any splice or any cinching loop.

* * * * *